United States Patent [19]
Höfling

[11] Patent Number: 5,364,356
[45] Date of Patent: Nov. 15, 1994

[54] SLEEVE CATHETER

[75] Inventor: Berthold Höfling, Wessling, Germany

[73] Assignee: Bavaria Medizin Technologie GmbH, Wessling/Oberpfaffenhofen, Germany

[21] Appl. No.: 132,877

[22] Filed: Oct. 7, 1993

[30] Foreign Application Priority Data

Jul. 19, 1993 [DE] Germany .............. 4324218

[51] Int. Cl.⁵ .................. A61M 29/00; A61M 25/00
[52] U.S. Cl. ..................... 604/96; 604/280
[58] Field of Search ............ 128/207.15; 604/52, 604/53, 105, 106, 96–101, 280; 606/191, 192, 194, 198

[56] References Cited

U.S. PATENT DOCUMENTS

| | | | |
|---|---|---|---|
| 4,693,243 | 9/1987 | Buras | 604/96 |
| 4,717,379 | 1/1988 | Ekholmer | 604/280 |
| 4,753,640 | 6/1988 | Nichols et al. | 604/280 |
| 5,021,044 | 6/1991 | Sharkawy | 604/280 |
| 5,049,132 | 9/1991 | Shaffer et al. | 604/96 |
| 5,146,916 | 9/1992 | Catalani | 128/207.15 |
| 5,257,974 | 11/1993 | Cox | 606/194 |
| 5,279,565 | 1/1994 | Hofling | 604/53 |

Primary Examiner—C. Fred Rosenbaum
Assistant Examiner—Frank Wilkens, III
Attorney, Agent, or Firm—Klaus J. Bach

[57] ABSTRACT

In a sleeve catheter for supplying medicine to the walls of a vessel or tubular organ in which a number of outer lumina extend longitudinally around a central lumen, the outer lumina have radial discharge openings in the area of the head portion of the catheter, which is slidable onto a balloon catheter in order to be disposed at least partially on the balloon of the balloon catheter so as to be expandable thereby into abutment with the inner wall of a vessel to be dilated whereby medicine can be supplied through the discharge openings in the outer lumina under pressure directly to the tissue of the vessel adjacent the outer lumina, thereby applying the medicine solely to the area engaged by the outer surface of the head portion.

5 Claims, 2 Drawing Sheets

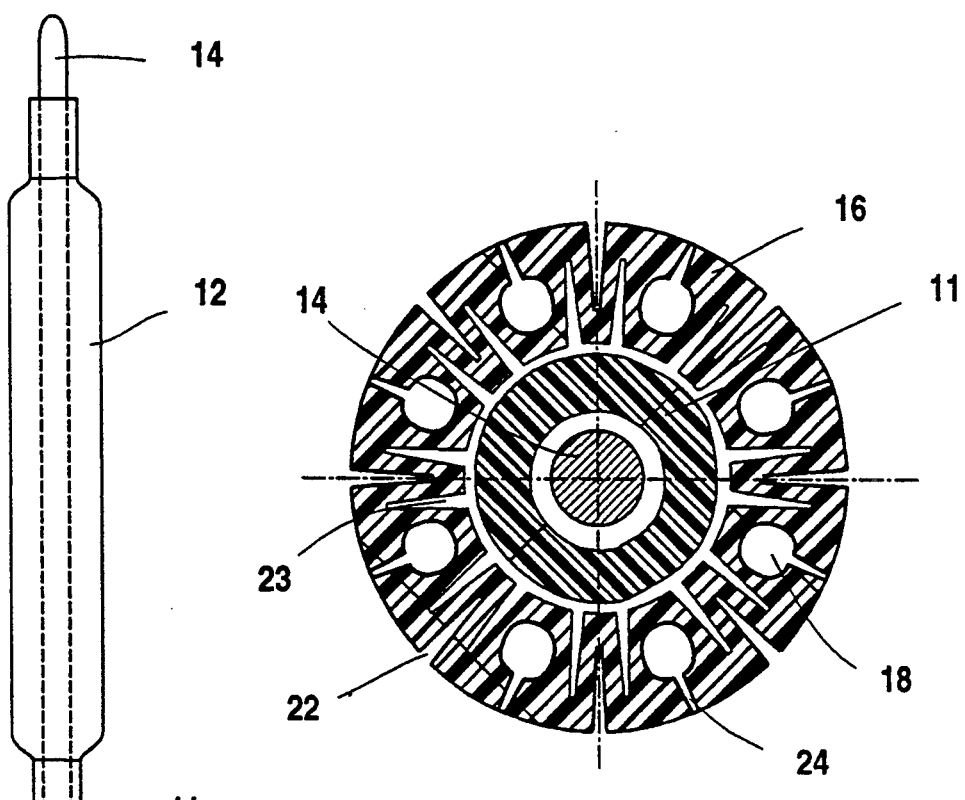
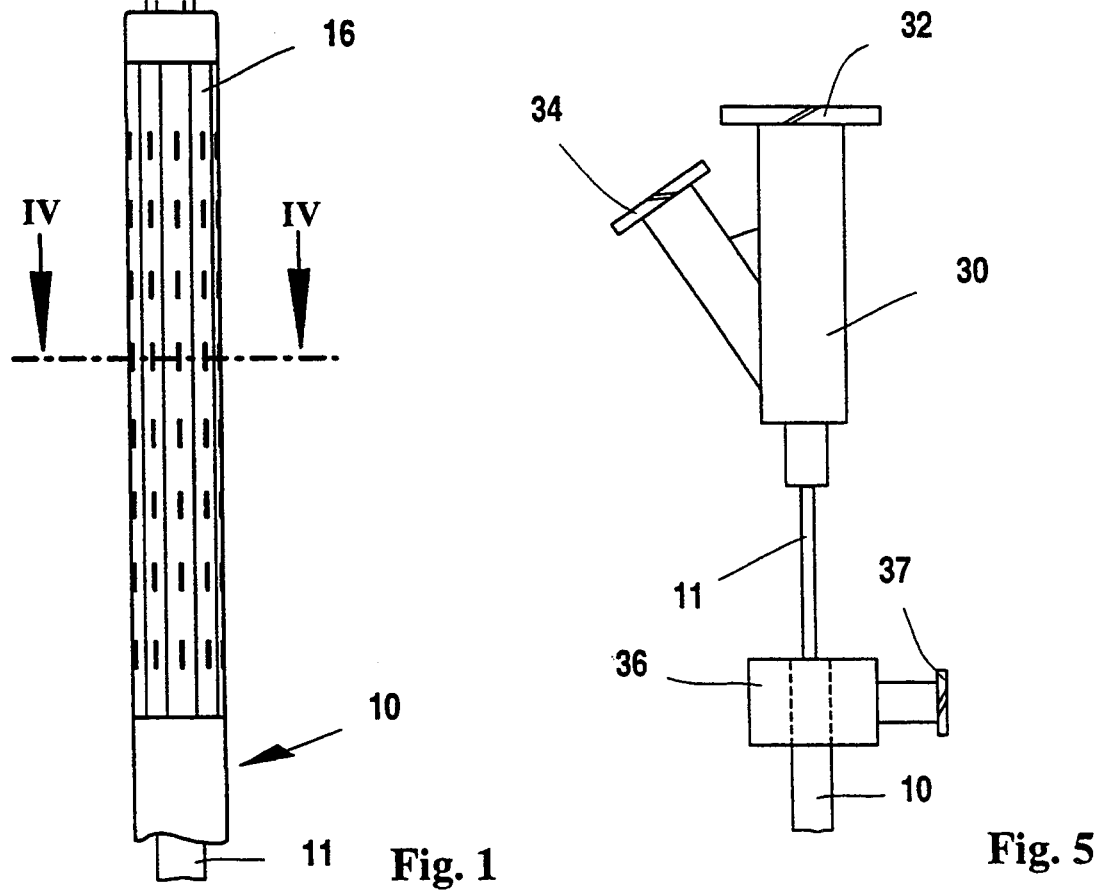

SLEEVE CATHETER

BACKGROUND OF THE INVENTION

The invention relates to a sleeve catheter for the wetting and infiltration of a vessel wall with a fluid particularly, medicine, preferably during routine treatment with a balloon catheter.

For the treatment of constricted passages in arteries, balloon dilation is recognized as an only little invasive but very effective and elegant method. Experience however shows that this treatment method has a high recurrence rate in the order of about 30% of the treated patients, that is, within a period of several months, for example, between 3 and 6 months, passage constriction will reoccur. It has been shown that this is at least partly caused by cell growth which is caused by the balloon dilation, that is, by expansion and rupture of the tissue. It is therefore desirable to provide the vessel area which is subjected to such balloon dilation additional treatment which counteracts such tissue growth.

Various methods for growth-inhibiting treatment are known, particularly, the application of energy, for example, by means of a laser or the localized treatment with special medicine. As carrier for the localized treatment with medicine it is known to use wire wall supports (so-called stents) whose use however is complicated and which cannot be removed.

It has also been proposed to use balloon catheters with perforated balloons so that, during the dilation procedure, medication can be administered for penetration into the tissue. However, this proposal was found to be unsuitable since already at the beginning of, and during, balloon expansion, uncontrollable amounts of medicine are lost so that it becomes impossible to apply a defined amount of medicine to the tissue wall areas to be treated for wetting of the tissue and infiltration into the tissue wall. During inflation of the balloon, that is, before the balloon wall abuts the vessel wall, a substantial amount of the medicine is released and this prematurely released amount of medicine does not reach the vessel layers to be treated and, consequently, an undesirably high dosage is required if the particular vessel area to be treated is to be exposed to a sufficient amount of medicine. Another disadvantage is seen in the fact that only an insufficient amount of pressure can be generated with a perforated balloon which may not be enough to expand the restricted vessel area.

It is desirable to overcome the disadvantages as described in connection with a perforated balloon, wherein however the effectiveness and the elegance of balloon dilation should be maintained and medication treatment of the tissue and the vessel wall should be facilitated during the same procedure without essential additional time input. It is therefore the object of the invention to improve the established balloon catheter procedure such that, on one hand, the high recurrence rate can be reduced by the simultaneous administration of medicine, and, on the other hand, the medicine is administered in the desired dosage and is applied essentially only to the tissue areas to be treated.

SUMMARY OF THE INVENTION

In a sleeve catheter fop supplying medicine to the walls of a vessel or tubular organ in which a number of outer lumina extend longitudinally around a central lumen, the outer lumina have radial discharge openings in the area of the head portion of the catheter, which is slidable onto a balloon catheter in order to be disposed at least partially on the balloon of the balloon catheter so as to be expandable thereby into abutment with the inner wall of a vessel to be dilated whereby medicine can be supplied through the discharge openings in the outer lumina under pressure directly to the tissue of the vessel adjacent the outer lumina, thereby applying the medicine solely to the area engaged by the outer surface of the head portion.

The arrangement according to the invention has the advantage that the sleeve catheter is slidable onto a portion of the deflated balloon of a balloon catheter, so that the low balloon profile as required for the insertion of the catheter into constricted vessel area is essentially maintained. Inflation of the balloon forces the head portion of the sleeve catheter into engagement with the tissue to be treated so that, during the dilation procedure the medicine can be applied, under pressure, through the outer lumina directly to the tissue to be treated whereby it enters solely this tissue. In this manner all toxic compounds or gene-technologically designated medicine adapted to inhibit undesirable cell growth in the treated area can be injected directly and only into the tissue area to be treated.

In a further embodiment according to the invention the perforations are preformed such that they are opened by application of the balloon pressure. They may also be preformed in such a manner that they are opened by the application of additional pressure to the outer lumina.

In order to facilitate the expansion of the head portion of the sleeve catheter, in another embodiment, the head portion is provided at its outside between the discharge openings with longitudinally extending radial notches. Expansion can be further facilitated by providing longitudinally extending radial notches also in the inner wall, between the outer lumina, which is disposed adjacent the inner lumen of the catheter.

In order to administer the medicine as locally as possible, that is, only in the close proximity of the constricted vessel area, or stenosis, it is advantageous if the discharge openings are preformed in such a manner that they are opened gradually with increasing pressure, beginning at the distal end, toward the proximal end of the head portion. Depending on the location where the sleeve catheter is to be used in connection with a balloon catheter, in vessels or in organs, it may be advantageous to administer different amounts of medicine for wetting the tissue or infiltration into the tissue. It is therefore within the scope of the present invention to provide distributed over the circumference of the head portion, six to twenty outer lumina.

BRIEF DESCRIPTION OF THE DRAWINGS

The advantages and features of the invention are apparent from the following description of an embodiment described below with reference to the drawings and defined in the claims.

FIG. 1 shows the head portion of a sleeve catheter disposed on a balloon catheter;

FIG. 4 is a cross-sectional view along lines IV—IV of FIG. 1; and FIG. 5 shows the connecting structure for the operation of the balloon catheter and the sleeve catheter.

DESCRIPTION OF THE PREFERRED EMBODIMENT

Figure 2:
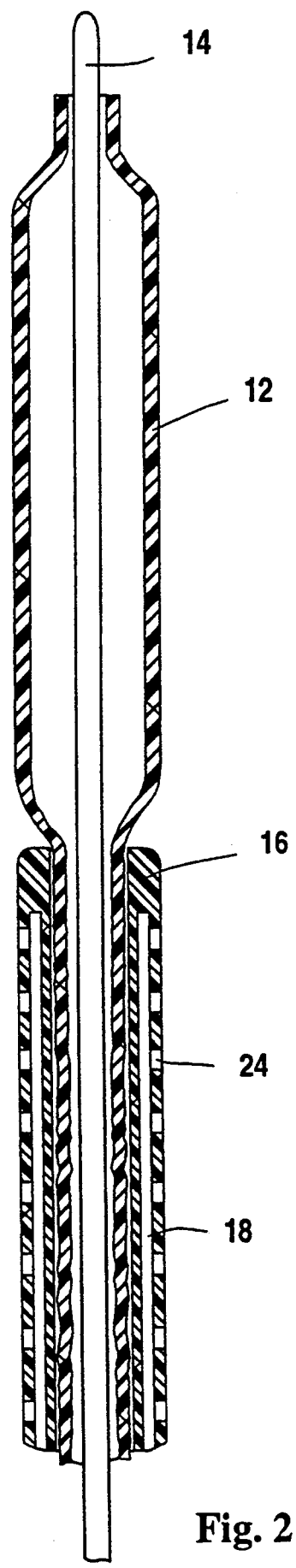
FIG. 2 is a cross-sectional view of the front end of the balloon catheter with the head portion of the sleeve catheter disposed thereon.
Figure 3:
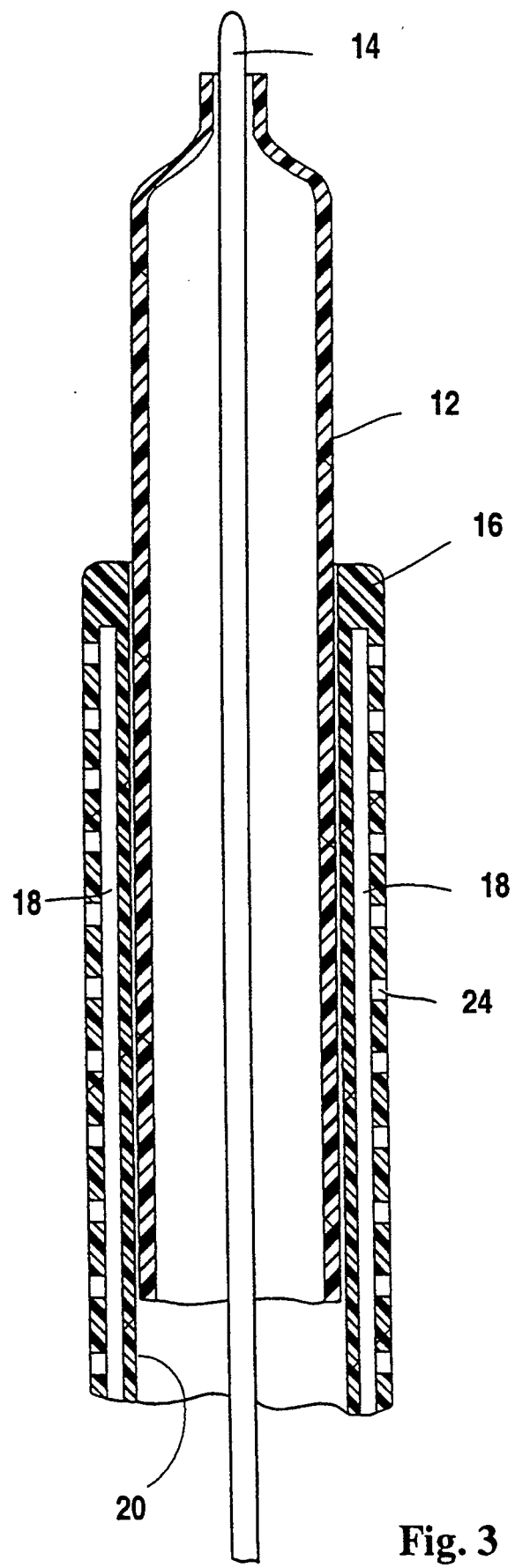
FIG. 3 is a cross-sectional view of the inflated balloon with an expanded head portion of the sleeve catheter.

FIGS. 1, 2 and 3 show the details of a sleeve catheter 10 disposed on a balloon catheter 11. The sleeve catheter is slipped onto the balloon catheter such that the head portion 16 extends at least partially over the balloon 12 which is mounted on a flexible guide rod 14 as shown in FIG. 2. In these relative positions the two catheters are inserted into a vessel or an organ. The outer lumina 18 terminate in the head portion of the sleeve catheter and they extend over the full length of the sleeve catheter up to the connecting structure which is shown in FIG. 5 and explained below. As shown the outer lumina 18 are arranged in a circle around a central lumen 20 wherein 6 to 20 outer lumina may be provided depending on the size and the application area of the sleeve catheter.

It is also possible to provide only one or two lumina which extend along the sleeve catheter and which are divided in the head portion into several outer lumina. The cross-section and the arrangement of the lumina are adapted to a particular application.

In the cross-sectional view of FIG. 4 which is taken across a head portion 16 disposed on a balloon catheter 11, there are eight outer lumina 18 which are provided with discharge openings 24 leading to the outside of the head portion. These discharge openings 24 are so designed that they open only toward the end of balloon pressure application and then discharge a medicine contained in the outer lumina 18. It is also possible to preform the discharge openings in such a way that they open only by application of additional pressure applied via the connecting structure.

In order to facilitate expansion of the head portion 16 it is provided, at least on the outside, with radial grooves 22 which extend longitudinally between the discharge openings 24 and to a limited depth spaced from the inner wall of the head portion so as to provide for a hinge structure allowing the radial grooves 22 to open up and expand the head portion with only small pressure requirements. In order to further reduce the pressure required for the expansion of the head portion 16 further radial grooves 23 may be provided at the inside of the head portion adjacent the central lumen 20, the grooves 23 extending longitudinally between the outer lumina 18. If two radial grooves 23 are provided at opposite sides of a radial groove 22, three-hinge structures are formed which further facilitate expansion of the head portion.

With this arrangement the head portion can be pressed in sufficiently tight contact with the vessel walls by the pressure of, for example, 5 to 8 bar required for full expansion of the balloon so that the medicine, when applied through the outer lumina 18 and the discharge openings 24, will not flow away but will be applied to the inner wall surface in a highly localized fashion such that it will penetrate the wall and then infiltrate the inner layers in sufficiently high concentrations.

For good distribution of the medicine during dilation when the head portion is firmly pressed against the expanded tissue by the pressure built up in the inner balloon, that is, in order to inject the medicine essentially in the center area of the constriction being treated, the discharge openings 24 are preferably preformed in such a manner that they open with increasing pressure beginning at the distal end of the head portion toward the proximal end. With this arrangement it is insured that the injected medicine is not carried away but is applied in sufficiently high concentration to the tissue layers as desired and subsequently infiltrates into the deeper wall layers. The amount of medicine released into the vessel after deflation of the catheter which normally takes place after about 60 seconds is then relatively small and it is diluted in a material way so that as far as the dose is concerned it is irrelevant for the total body system even if a large dose was applied localized to the treated vessel area. For application, primarily already well known cell-toxic compounds are used whose effects can be well determined but also genetically designed medicine may be used.

Utilization of pressure generators (indeflator) as normally used in connection with balloon dilation permits injection and infiltration of medicine into the tissue under any desired pressure and in any desired predetermined amount.

FIG. 5 shows a connecting structure for an indeflator and for an operating mechanism for injecting a medicine. The connecting structure comprises a Y connector with a terminal 32 for scavenging and a terminal 34 for the indeflator. The balloon catheter 11 is connected to this Y connector. The sleeve catheter 10 which surrounds the balloon catheter 11 is provided at its rear end with a connecting structure 36 which has a terminal 37 through which the medicine is supplied by means of a pressurizer which is not shown in the drawing. Within the connecting structure 36 the terminal 37 is connected to the outer lumina 18 of the sleeve catheter.

With this connecting structure arrangement the balloon dilation can be performed independently of the application of the medicine so that the medicine can be administered independently and in predetermined amounts.

For the treatment of coronary vessels the invention provides fop a substantial advantage in that the elegance of the balloon dilation method is maintained and the procedure is not extended because the medicine is injected during the normal dilation procedure during which, furthermore, an exactly defined amount of medicine is administered within a well determined vessel area.

However the arrangement according to the invention is suitable not only fop treatment of coronary vessels but also fop kidney vessels and vessels in extremities and, depending on the conditions, also for vessels in the head of a patient. It may also be used For the wetting and infiltration of growth-inhibiting compounds in vessel portions of organs or tubular systems such as the urethra or the bile duct or other vessel-like organs. The arrangement according to the invention is also particularly well suited for the treatment of cancerous areas with growth-inhibiting compounds (in this case cytostatics). The arrangement further permits treatment of tubular structures riddled with carcinoma without endangering or blocking passage therethrough that is also malicious sicknesses in the area of the trachea or the intestines can be treated in accordance with the invention without disturbing passage through the affected areas. Also for the treatment prostate hypertrophy medicine can be administered in the described manner.

What is claimed is:

1. A sleeve catheter for the wetting and infiltration of a vessel wall or other tubular organ by a fluid, particularly a liquid medicine, said sleeve catheter comprising a head portion with a central lumen and a number of outer lumina extending, in cross-section, in a circle around said central lumen, each having discharge openings formed in the head portion thereof, said sleeve catheter having, during operation, a balloon catheter arranged therewithin so as to be disposed at lead partially on the balloon of said balloon catheter, said head portion of said sleeve catheter including, at its outside, longitudinally extending radial grooves arranged between said discharge openings and extending to a limited depth so as to provide adjacent the inner wall of said sleeve catheter for a hinge structure allowing said radial grooves to open so as to facilitate expansion of said sleeve catheter for engaging the inner wall of a vessel to be expanded upon inflation of said balloon, and said discharge openings being preformed such that they open only upon expansion of said sleeve catheter by the application of the balloon pressure, and means for supplying said fluid to said outer lumina under pressure so as to be applied to said vessel wall via said discharge openings when said head portion is expanded into engagement with the inner vessel wall to be treated.

2. A sleeve catheter according to claim 1, wherein said discharge openings are preformed such that they are opened by the application of an additional pressure to the outer lumina.

3. A sleeve catheter according to claim 1, wherein longitudinally extending radial grooves are provided between said outer lumina also in the inner wall of said lead portion adjacent the central lumen and extend from the inner wall to a limited depth adjacent the outer wall of said sleeve catheter so as to form at said outer wall a hinge structure allowing said grooves to open so as to further facilitate expansion of said sleeve catheter.

4. A sleeve catheter according to claim 1, wherein said discharge openings are preformed in such a way that they are opened successively with increasing pressure beginning at the distal end of the head portion and continuing toward the proximal end of the head portion.

5. A sleeve catheter according to claim 1, wherein said head portion includes six to twenty outer lumina distributed over its circumference.

* * * * *